United States Patent
Maskara et al.

(10) Patent No.: US 10,201,289 B2
(45) Date of Patent: *Feb. 12, 2019

(54) MEASURING ATRIAL FIBRILLATION BURDEN USING IMPLANTABLE DEVICE BASED SENSORS

(71) Applicant: Cardiac Pacemakers, Inc., St. Paul, MN (US)

(72) Inventors: Barun Maskara, Blaine, MN (US); Pramodsingh Hirasingh Thakur, Woodbury, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,600

(22) Filed: Jan. 10, 2017

(65) Prior Publication Data

US 2017/0143223 A1    May 25, 2017

Related U.S. Application Data

(63) Continuation of application No. 14/539,424, filed on Nov. 12, 2014, now Pat. No. 9,591,986.
(Continued)

(51) Int. Cl.
*A61N 1/365*    (2006.01)
*A61B 5/046*    (2006.01)
(Continued)

(52) U.S. Cl.
CPC .......... *A61B 5/046* (2013.01); *A61B 5/04012* (2013.01); *A61B 5/0456* (2013.01);
(Continued)

(58) Field of Classification Search
CPC ............ A61N 1/36585; A61N 1/36521; A61N 1/36592; A61N 1/3624; A61B 5/04012; A61B 5/0452; A61B 5/046
See application file for complete search history.

(56) References Cited

U.S. PATENT DOCUMENTS

| | | |
|---|---|---|
| 4,773,401 A | 9/1988 | Citak et al. |
| 5,042,497 A | 8/1991 | Shapland |

(Continued)

FOREIGN PATENT DOCUMENTS

WO    WO-2015088695 A1    6/2015

OTHER PUBLICATIONS

"U.S. Appl. No. 14/539,424, Advisory Action dated Apr. 15, 2016", 4 pgs.
(Continued)

*Primary Examiner* — William J Levicky
(74) *Attorney, Agent, or Firm* — Schwegman Lundberg & Woessner, P.A.

(57) ABSTRACT

An apparatus may include a sensing circuit and an arrhythmia detection circuit. The sensing circuit is configured to generate a sensed physiological signal representative of cardiac activity of a subject. The arrhythmia detection circuit is configured to monitor ventricular depolarization (V-V) intervals using the sensed physiological signal, detect when at least a portion of the V-V intervals satisfies an arrhythmia detection threshold interval, calculate a value of variability of the V-V intervals and calculate a value of variability of a systolic portion of the V-V intervals in response to the detection, and generate an indication of atrial fibrillation (AF) according to a comparison including the value of variability of the V-V intervals and the value of variability of the systolic portion of the V-V intervals and provide the indication to at least one of a user or process.

20 Claims, 5 Drawing Sheets

Related U.S. Application Data (60) Provisional application No. 61/914,026, filed on Dec. 10, 2013.

(51) Int. Cl.
    *A61B 5/04*     (2006.01)
    *A61N 1/39*     (2006.01)
    *A61N 1/362*     (2006.01)
    *A61B 5/0456*     (2006.01)
    *A61B 7/02*     (2006.01)

(52) U.S. Cl.
    CPC ............ *A61B 7/023* (2013.01); *A61N 1/3624* (2013.01); *A61N 1/36585* (2013.01); *A61N 1/36592* (2013.01); *A61N 1/3925* (2013.01); *A61N 1/3956* (2013.01); *A61N 1/3987* (2013.01); *A61N 1/36521* (2013.01)

(56) References Cited

U.S. PATENT DOCUMENTS

| | | | |
|---|---|---|---|
| 6,076,015 | A | 6/2000 | Hartley et al. |
| 7,369,890 | B2 | 5/2008 | Lovett |
| 7,925,348 | B1 | 4/2011 | Bornzin et al. |
| 8,244,355 | B2 | 8/2012 | Bennett et al. |
| 2004/0127792 | A1 | 7/2004 | Siejko et al. |
| 2007/0142866 | A1 | 6/2007 | Li |
| 2010/0113889 | A1 | 5/2010 | Ghanem |
| 2011/0184301 | A1 | 7/2011 | Holmström et al. |
| 2012/0253207 | A1 | 10/2012 | Sarkar et al. |
| 2012/0296228 | A1 | 11/2012 | Zhang et al. |
| 2015/0157229 | A1 | 6/2015 | Maskara et al. |

OTHER PUBLICATIONS

"U.S. Appl. No. 14/539,424, Examiner Interview Summary dated Apr. 12, 2016", 5 pgs.

"U.S. Appl. No. 14/539,424, Examiner Interview Summary dated Oct. 14, 2016", 3 pgs.

"U.S. Appl. No. 14/539,424, Final Office Action dated Feb. 16, 2016", 19 pgs.

"U.S. Appl. No. 14/539,424, Non Final Office Action dated Jul. 14, 2016", 11 pgs.

"U.S. Appl. No. 14/539,424, Non Final Office Action dated Oct. 6, 2015", 19 pgs.

"U.S. Appl. No. 14/539,424, Notice of Allowance dated Oct. 27, 2016", 18 pgs.

"U.S. Appl. No. 14/539,424, Response filed Apr. 5, 2016 to Final Office Action dated Feb. 16, 2016", 13 pgs.

"U.S. Appl. No. 14/539,424, Response filed May 4, 2016 to Final Office Action dated Feb. 16, 2016", 13 pgs.

"U.S. Appl. No. 14/539,424, Response filed Oct. 11, 2016 to Final Office Action dated Jul. 14, 2016", 9 pgs.

"U.S. Appl. No. 14/539,424, Response filed Dec. 30, 2015 to Non Final Office Action dated Oct. 6, 2015", 13 pgs.

"international Application Serial No. PCT/US2014/065230, International Preliminary Report on Patentability dated Jun. 23, 2016", 8 pgs.

"International Application Serial No. PCT/US2014/065230, International Search Report dated Feb. 11, 2015", 4 pgs.

"International Application Serial No. PCT/US2014/065230, Written Opinion dated Feb. 11, 2015", 6 pgs.

Tavel, Morton E., et al., "Left Ventricular Ejection Time in Atrial Fibrillation", Circulation, (1972), 744-752.

MEASURING ATRIAL FIBRILLATION BURDEN USING IMPLANTABLE DEVICE BASED SENSORS

CLAIM OF PRIORITY

This application is a continuation of U.S. application Ser. No. 14/539,424, filed Nov. 12, 2014, which claims the benefit of priority under 35 U.S.C. § 119(e) of U.S. Provisional Patent Application Ser. No. 61/914,026, filed on Dec. 10, 2013, which is herein incorporated by reference in its entirety.

BACKGROUND

Implantable medical devices (IMDs) include devices designed to be implanted into a patient. Some IMDs are designed to provide electrical cardiac therapy to a patient or subject, such as cardiac function management (CFM) devices such as implantable pacemakers, implantable cardioverter defibrillators (ICDs), cardiac resynchronization therapy devices (CRTs), and devices that include a combination of such capabilities for example. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and include electrodes that are able to sense cardiac signals without being in direct contact with the patient's heart. Other examples of IMDs include implantable diagnostic devices such as implantable loop recorders, implantable drug delivery systems, or implantable devices with neural stimulation capability.

IMDs can be single chamber devices (e.g., single chamber ICD) that sense cardiac signals and deliver therapy to a single heart chamber (e.g., the right ventricle) and do not include dedicated atrial sensing capability. Additionally, some diagnostic-only devices do not include dedicated atrial sensing capability. However, patients with these types of devices may develop atrial arrhythmias, such as atrial fibrillation (AF) for example. Knowledge of the amount of time or percentage of time that the patient spends in AF (AF burden) can be useful to physicians for effective titration of drug therapy, especially for heart failure patients who typically have a high incidence of AF.

OVERVIEW

This document discusses systems, devices and methods for improved discrimination of atrial arrhythmia. An apparatus example can include a sensing circuit and an arrhythmia detection circuit. The sensing circuit is configured to generate a sensed physiological signal representative of cardiac activity of a subject. The arrhythmia detection circuit is configured to monitor ventricular depolarization (V-V) intervals using the sensed physiological signal, detect when at least a portion of the V-V intervals satisfies an arrhythmia detection threshold interval, calculate a value of variability of the V-V intervals and calculate a value of variability of a systolic portion of the V-V intervals in response to the detection, and generate an indication of atrial fibrillation (AF) according to a comparison including the value of variability of the V-V intervals and the value of variability of the systolic portion of the V-V intervals and provide the indication to at least one of a user or process.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An ambulatory medical device may include one or more of the features, structures, methods, or combinations thereof described herein. For example, a cardiac monitor or cardiac stimulator may be implemented to include one or more of the advantageous features or processes described below. It is intended that such a monitor, stimulator, or other implantable, subcutaneously implantable, partially implantable device, or wearable device need not include all of the features described herein, but may be implemented to include selected features that provide for unique structures or functionality. Such a device may be implemented to provide a variety of therapeutic or diagnostic functions.

As explained previously, it may be desirable to accurately assess the AF burden of patient or subject, but the patient may be prescribed a device that does not have electrodes dedicated for atrial sensing.

Figure 1:
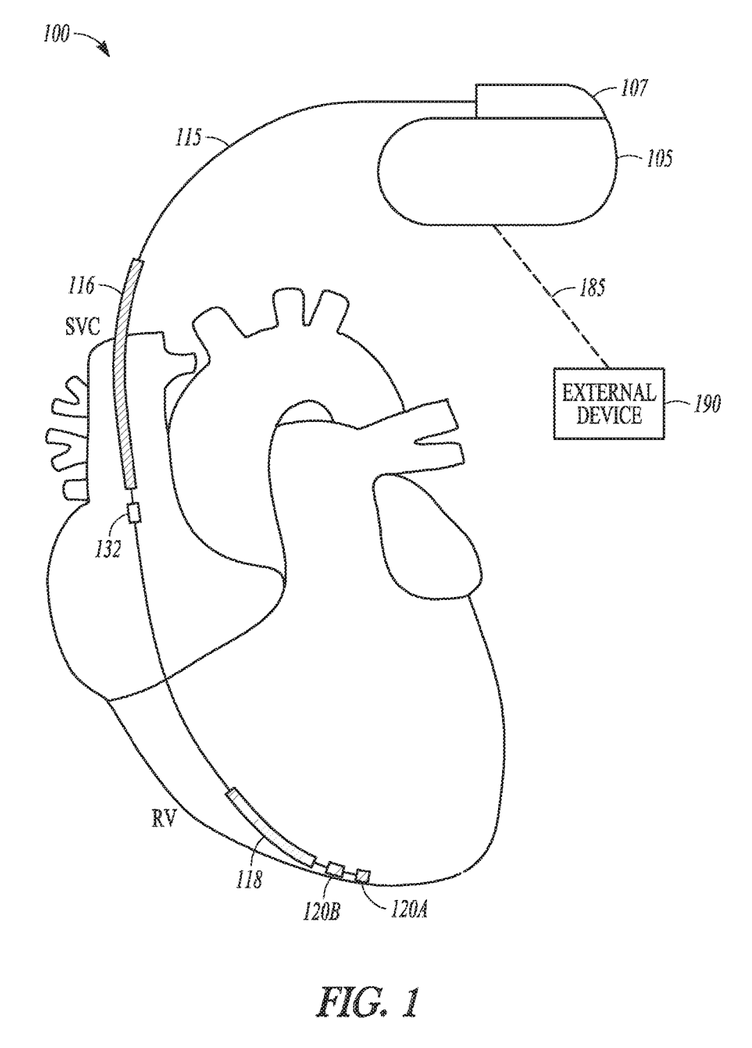
FIG. 1 is an illustration of an example of portions of a system that includes an IMD.

FIG. 1 is an illustration of an example of portions of a system 100 that includes an IMD 105. Examples of IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart. The RV tip electrode 120A, RV ring electrode 120B, or an electrode formed on the can of IMD 105 allow for sensing an RV electrogram signal representative of RV depolarizations and delivering RV pacing pulses. The IMD 105 includes a sense amplifier circuit to provide amplification or filtering of the sensed signal. Sensing and pacing allows the IMD 105 to adjust timing of the heart chamber contractions.

Some IMDs, such as shown in FIG. 1, may not include any electrodes for sensing electrical activity in an atrium. For example, the IMD 105 can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and/or depolarization signal morphology analysis).

The IMD 105 may be a diagnostic-only device and not provide electrical therapy to the patient. Such a device may include a combination of the RV tip electrode 120A, RV ring electrode 120B, or the electrode formed on the can of IMD 105 allow for sensing ventricular depolarizations. The IMD 105 may be implantable subcutaneously and may include electrodes that can sense ventricular depolarization (e.g., using far-field sensing), but not include lead electrodes that directly contact the heart. Other examples of the IMD 105 include a loop recorder, a diagnostic device without leads in the heart, a leadless pacemaker, a neurostimulator (including but not limited to vagus nerve stimulators, baroreceptor stimulators, and spinal cord stimulators), or other IMD without a electrode positioned in the atrium.

The absence of dedicated sensing for intrinsic atrial depolarizations (P-waves) may make it difficult for a clinician to retrospectively diagnose atrial arrhythmia such as AF. Yet, a device-based estimate of the AF burden can be useful to a clinician to determine which anti-arrhythmic therapy or therapies to use, or which anticoagulant therapy or therapies to prescribe.

Figure 2:
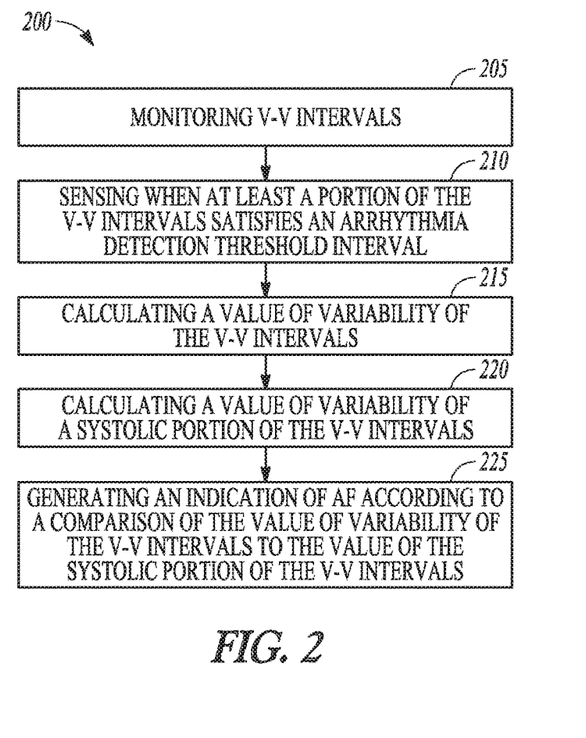
FIG. 2 is a flow diagram of an example of a method of operating a medical device to detect and classify atrial arrhythmia.

FIG. 2 is a flow diagram of an example of a method 200 of operating an ambulatory medical device, which does not have a dedicated atrial sensing circuit, to detect and classify atrial arrhythmia. The device may be implantable or wearable. At block 205, ventricular depolarization (V-V) intervals of a subject are monitored. The intervals may be monitored using a sensed cardiac signal indicative of electrical cardiac activity of the subject (e.g., an electrogram signal or electrocardiogram signal), or may be monitored using a different type of sensed signal, such as a physiologic impedance signal representative of intracardiac impedance or thoracic impedance of the subject for example. V-V intervals may be determined for example by monitoring a fiducial of the impedance signal, such as a maximum, minimum, or other fiducial of the impedance signal.

In some variations, the V-V intervals can be monitored using a heart sound signal. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the end of systole. The third heart sound (S3) and fourth heart sound (S4) are related to filling pressures of the left ventricle during diastole. A heart sound signal includes a representation of one or more of the heart sounds. V-V intervals may be determined for example by monitoring a fiducial of the heart sound signal, such as a fiducial indicating the S1 heart sound or the S2 heart sound for example.

In certain examples, the device senses when at least a portion of the V-V intervals satisfy a specified arrhythmia detection threshold interval value, such as shown at block 210. In certain examples, the device determines when X of Y intervals satisfy the arrhythmia detection threshold (e.g., when 8 of 10 intervals satisfy the arrhythmia detection threshold).

At block 215, the device calculates a value of variability of the V-V intervals. In some examples, the value of variability is calculated when arrhythmia is detected. In some examples, the value of variability is detected periodically. Variability may be determined as a standard deviation of the V-V intervals. In another example, variability may be determined using values of pair-wise differences of consecutive V-V intervals (ΔV-V). The variability measurement can be initialized using an average of a specified number (e.g., four) of V-V interval differences. When a new V-V interval is detected, a current difference in the V-V interval is calculated and the variability measurement can be calculated as the current difference minus the average of the previous differences.

At block 220, the device determines a systolic portion of the V-V intervals and calculates a value of variability of a systolic portion of the V-V intervals. The systolic portion of a V-V interval can be called a systolic time interval or STI. The systolic portion corresponds to the portion of the depolarization interval associated with ejection of blood from the ventricles. The diastolic portion of the V-V intervals is associated with filling of the ventricles. An example of an STI (as discussed further in regard to FIGS. 3 and 4) is the interval between an R-wave (indicating a portion of depolarization of the ventricles) and the S2 heart sound (indicating the end of systole) or the R-S2 interval.

At block 225, an indication of AF can be generated by the device according to a comparison that includes the value of variability of the V-V intervals and the value of variability of the STI's. The indication may be an alert to a user (e.g., a patient or a caregiver) or the indication may be a signal communicated to initiate another process associated with detection of AF.

Figure 3:
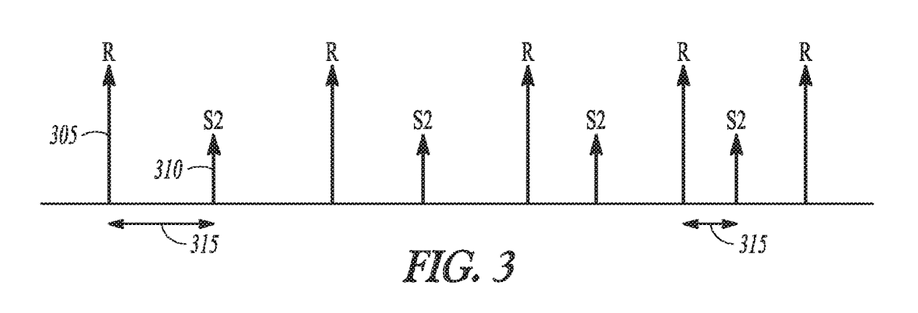
FIG. 3 illustrates an example of ventricular depolarization intervals and systolic time intervals for normal sinus rhythm.

FIG. 3 illustrates an example of V-V intervals and STI's for normal sinus rhythm. The taller arrows 305 represent timing of an R-wave and the shorter arrows 310 represent timing of an S2 heart sound. A V-V interval (or R-R interval) is therefore represented by the interval between two tall arrows and an STI is represented by an interval between a taller arrow and a shorter arrow (R-S2 interval 315). In a normal rhythm, STI's are inversely related to heart rate. The Figure shows that as the sinoatrial (SA) node of the heart drives the heart rate higher (as represented by decreasing intervals between the taller arrows or decreasing R-R intervals), the STI decreases with the higher heart rate (as shown by decreasing R-S2 intervals).

Figure 4:
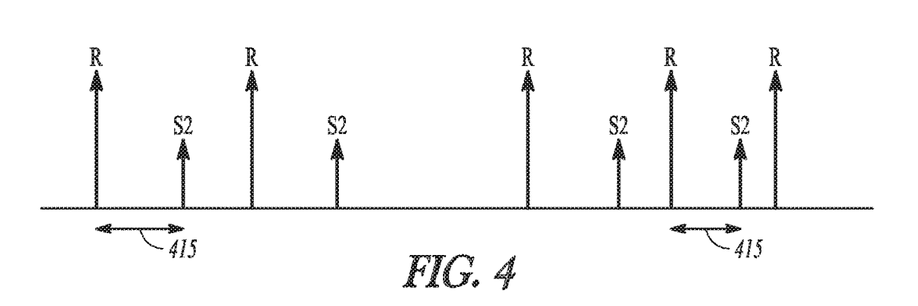
FIG. 4 illustrates an example of ventricular depolarization intervals and systolic time intervals for atrial fibrillation.

FIG. 4 illustrates an example of V-V intervals and STI's for AF. When a heart is in AF, the STI's 415 tend to plateau at a higher heart rate and do not continue to decrease as the heart rate increases. FIG. 4 shows that as the V-V interval varies with AF, the value of the STI plateaus so that the value of the STI does not continue to decrease as the V-V interval decreases. Therefore, detecting a highly variable V-V interval with little or no change in variability in STI may indicate AF.

Figure 5:
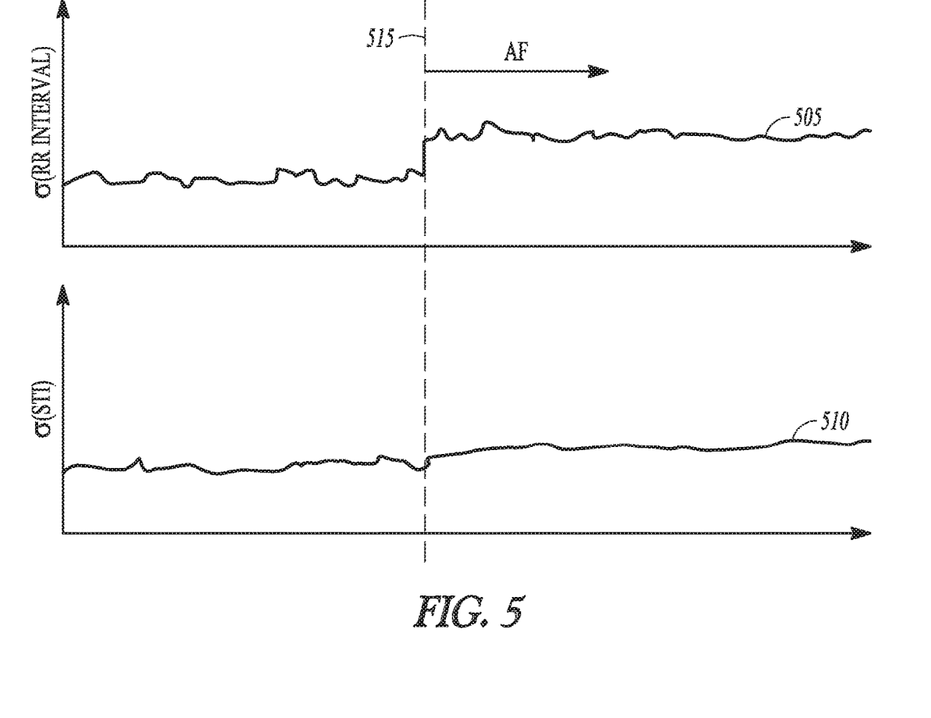
FIG. 5 illustrates an example of a graph of variability of ventricular depolarization intervals and an example of a graph of variability of a standard deviation of systolic time intervals.

FIG. 5 illustrates an example of a graph 505 of a standard deviation a of V-V intervals (or R-R intervals) and an example of a graph 510 of a standard deviation of STI's. The vertical dashed line 515 indicates onset of AF. As can be seen in the graphs, the variability in the V-V interval increases during an episode of AF while the variability of the ST interval changes much less. Therefore, a sudden change in V-V interval variability with respect to STI variability can indicate the onset of AF.

Figure 6:
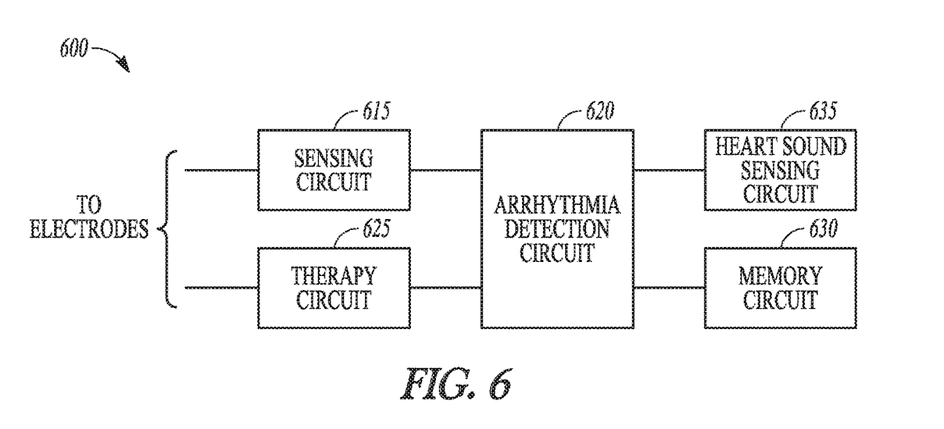
FIG. 6 is a block diagram of portions of an example of a medical device to detect and classify atrial arrhythmia.

FIG. 6 is a block diagram of portions of an example of an ambulatory medical device 600 to detect and classify atrial arrhythmia. The ambulatory medical device may be implantable, partially implantable, or wearable and non-implantable. The device 600 may include a therapy circuit 625 that provides electrical cardioverter/defibrillation therapy and/or pacing stimulation energy to a single ventricle of the subject. The device 600 may be implantable subcutaneously and include electrodes configured to sense cardiac signals absent direct cardiac contact with the subject. The device 600 may be an implantable loop recorder and include a memory circuit 630 that can record cardiac activity of the subject over multiple days. The device may be a diagnostic patch or garment worn by a patient for post-hospitalization monitoring.

The device 600 can include a sensing circuit 615 that generates a sensed physiological signal representative of cardiac activity of the patient or subject. The device 600 can also include an arrhythmia detection circuit 620. The arrhythmia detection circuit 620 can include one or more of hardware, software, and firmware. For instance, the arrhythmia detection circuit 620 may include a processor (e.g., a microprocessor) executing instructions in one or more software or firmware modules. The arrhythmia detection circuit 620 may include can include hardware such as logic circuits to perform at least part of the functions described. The arrhythmia detection circuit 620 can be configured to perform the functions described by configuring one or more of the hardware, software, and firmware.

The arrhythmia detection circuit 620 monitors V-V intervals using the sensed physiological signal and detects when at least a portion of the V-V intervals satisfy an arrhythmia detection threshold interval. In certain examples, the arrhythmia detection circuit 620 detects tachyarrhythmia when the V-V intervals are less than a specified (e.g., programmed) largest tachyarrhythmia detection interval value. The arrhythmia detection circuit 620 calculates a value of variability of the V-V intervals and calculates a value of variability of a systolic portion of the V-V intervals in response to the detection of the arrhythmia. In certain examples, the arrhythmia detection circuit 620 first calculates a value of variability of the V-V intervals and detects arrhythmia using the calculated variability. The arrhythmia detection circuit 620 then calculates the value of variability of a systolic portion of the V-V intervals.

The arrhythmia detection circuit 620 generates an indication of AF according to a comparison including the value of variability of the V-V intervals and the value of variability of the systolic portion of the V-V intervals, or according to the variability of the V-V intervals alone. In some examples, the arrhythmia detection circuit 620 compares the value of variability of the V-V intervals to a first specified arrhythmia detection variability value threshold (TH1) and compares the value of variability of the systolic portion of the V-V intervals to a second specified arrhythmia detection variability value threshold (TH2). The arrhythmia detection circuit 620 may generate the indication of AF when the value of variability of the V-V intervals satisfies the first specified arrhythmia detection threshold (e.g., $\Delta\sigma(V\text{-}V) > TH1$) and the value of variability of the systolic portion of the V-V intervals does not satisfy the second specified arrhythmia detection threshold (e.g., $\Delta\sigma(STI) < TH2$).

In some examples, the arrhythmia detection circuit 620 calculates a ratio of the value of variability of the V-V intervals to the value of variability of the STI's (e.g., ratio=$\Delta\sigma(V\text{-}V)/\Delta\sigma(STI)$). The arrhythmia detection circuit 620 generates the indication of AF when the calculated ratio satisfies a specified AF detection ratio threshold value. Thus, the value of the ratio will increase during AF when the variability of the V-V intervals may be large while the variability of the STI's may be small.

The arrhythmia detection circuit 620 may generate the indication of AF when detecting a significant change in V-V interval variability that occurs suddenly with respect to the STI variability. For instance, the arrhythmia detection circuit may detect when a change in the variability of the V-V intervals satisfies a specified arrhythmia detection variability change value threshold within a specified time duration. The time duration may be determined using a timer circuit or determined as a number of V-V intervals. The arrhythmia detection circuit 620 may compare the value of variability of the V-V intervals to the value of variability of the STI's when the change in the variability of the V-V intervals satisfies the conditions for value and time.

Different approaches can be used to measure the intervals. In some examples, the implantable sensing circuit 615 includes a cardiac signal sensing circuit and the sensed physiological signal is representative of electrical cardiac activity of the subject. The arrhythmia detection circuit 620 may include a peak detector circuit and may measure the V-V intervals by detecting peaks associated with the R-wave of depolarization complexes. The device 600 may also include a heart sound sensing circuit 635. The heart sound sensing circuit 635 can generate a sensed heart sound signal representative of at least one heart sound of the subject.

The heart sound sensing circuit 635 can be disposed in a heart, or near the heart in a location where the acoustic energy of the heart sound can be sensed. The heart sound sensor can include an accelerometer disposed in or near a heart. The heart sound sensor can include a microphone disposed in or near a heart. An approach for monitoring heart sounds can be found in Siejko et al., U.S. Patent Application Publ. No. 2004/0127792, entitled "Method and Apparatus for Monitoring of Diastolic Hemodynamics," filed Dec. 30, 2002, which is incorporated herein by reference.

The STI can include at least one fiducial in the sensed heart sound signal. In certain examples, the arrhythmia detection circuit 620 monitors an STI that includes the time interval from an R-wave sensed by the cardiac signal sensing circuit to an S2 heart sound sensed using the heart sound sensing circuit 635 (R-S2 interval). In certain examples, the arrhythmia detection circuit 620 monitors an STI that includes the time interval from an R-wave to an S1 heart sound (R-S1 interval). In certain examples, the arrhythmia detection circuit 620 monitors an STI that includes the time interval from a Q-wave to an S2 heart sound (Q-S2 interval). A Q-wave is the onset of a QRS complex that is associated with the onset of ventricular depolarization. In certain examples, the arrhythmia detection circuit 620 monitors an STI that includes the time interval from a Q-wave to an S1 heart sound (Q-S1 interval). In certain examples, the arrhythmia detection circuit 620 monitors an STI that includes the time interval from an S1 heart sound to the S2 heart sound (S1-S2 interval).

In some examples, the implantable sensing circuit 615 includes an impedance sensing circuit and the sensed physiological signal is an impedance signal representative of physiologic impedance of the subject. In certain examples, the implantable sensing circuit 615 includes an intracardiac impedance sensing circuit. Electrodes may be placed within the right ventricle of the heart to obtain a signal of intracardiac impedance versus time. The intracardiac impedance signal waveform can be signal processed to obtain a measure of one or both of the V-V time interval time interval and the STI using specified fiducials of the intracardiac impedance signal. An approach to measuring intracardiac impedance is described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety.

In certain examples, the implantable sensing circuit 615 includes a thoracic impedance sensing circuit. Electrodes may be placed across at least a portion of the thorax region of the subject to obtain a signal of thoracic impedance versus time. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety.

Figure 7:
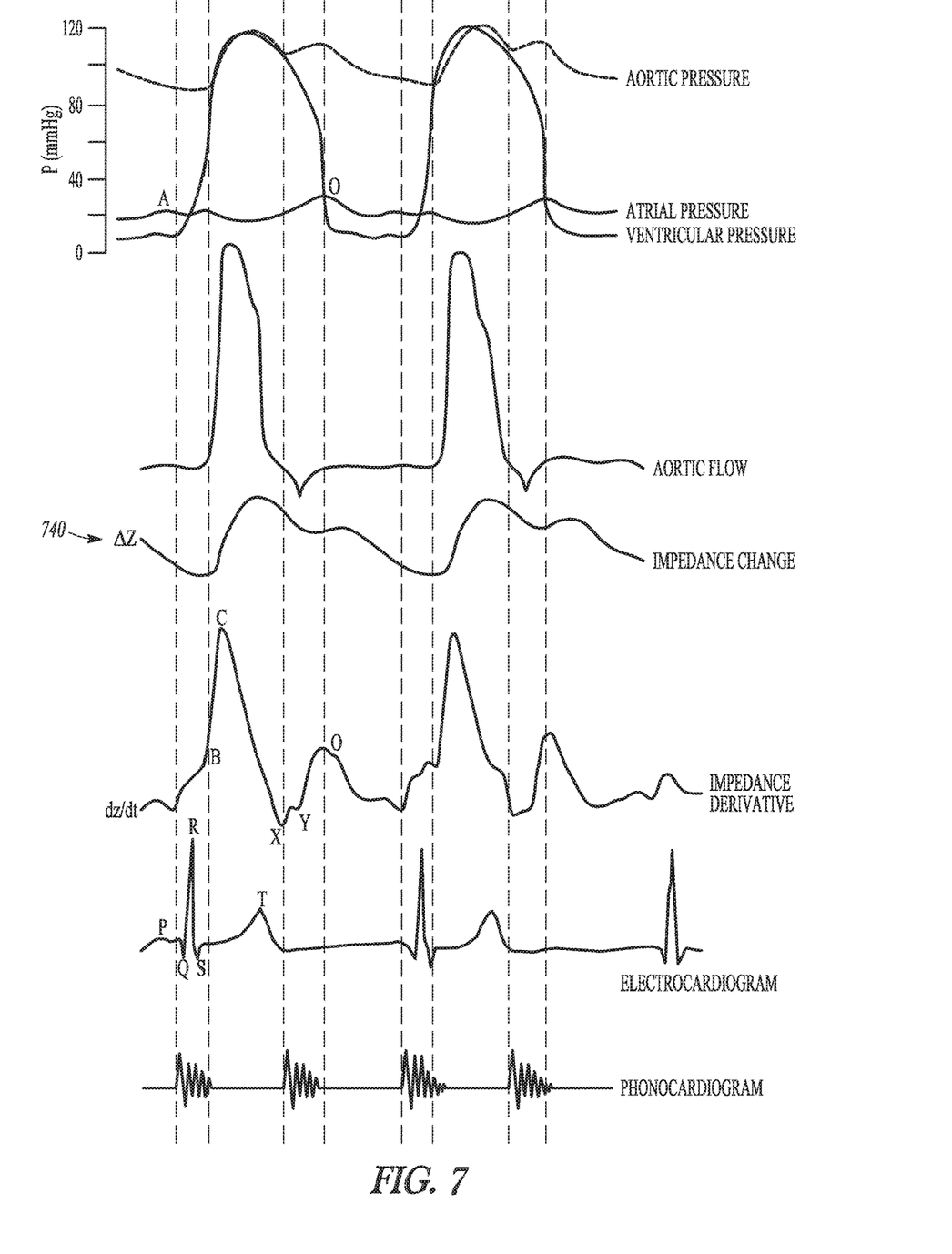
FIG. 7 shows examples of sensed physiologic signals.

FIG. 7 shows examples of sensed physiologic signals including an intracardiac impedance signal 740. The arrhythmia detection circuit 620 of FIG. 6 may monitor the V-V intervals using a fiducial in the impedance signal. For example, the arrhythmia detection circuit 620 may measure a V-V interval as the time duration between minimums of the intracardiac impedance signal 740. The arrhythmia detection circuit 620 may monitor an STI that includes a time interval between fiducials in the sensed impedance signal that are associated with the systolic portion of the V-V intervals. In certain examples, the arrhythmia detection circuit 620 monitors an STI that includes a time interval between a minimum and a maximum of the impedance signal. In certain examples, the arrhythmia detection circuit 620 monitors an STI that includes a time interval between a minimum of the impedance signal and a peak value of slope of the impedance signal. In certain examples, the arrhythmia detection circuit 620 monitors an STI that includes a time interval between a first fiducial indicative of a minimum slope of the impedance signal prior to the peak value of slope and a second fiducial indicative of a minimum value of the impedance signal after the peak value of slope. The arrhythmia detection circuit 620 may monitor the V-V intervals and STI's using a combination of cardiac activity signal and impedance signal. For instance, the arrhythmia detection circuit 620 may monitor V-V intervals as the interval between R-waves in an electrocardiogram and monitor STI's using one or more fiducials of the impedance signal.

The indication of AF may be provided to at least one of a user or process. The device 600 may include a memory circuit 630 integral to or in electrical communication with the arrhythmia detection circuit 620. The arrhythmia detection circuit 620 may use indications of AF to calculate a value of AF burden for the subject. In certain examples, there may be multiple processes executing on a processor of the device and the indication may be a signal communicated between the processes.

Figure 8:
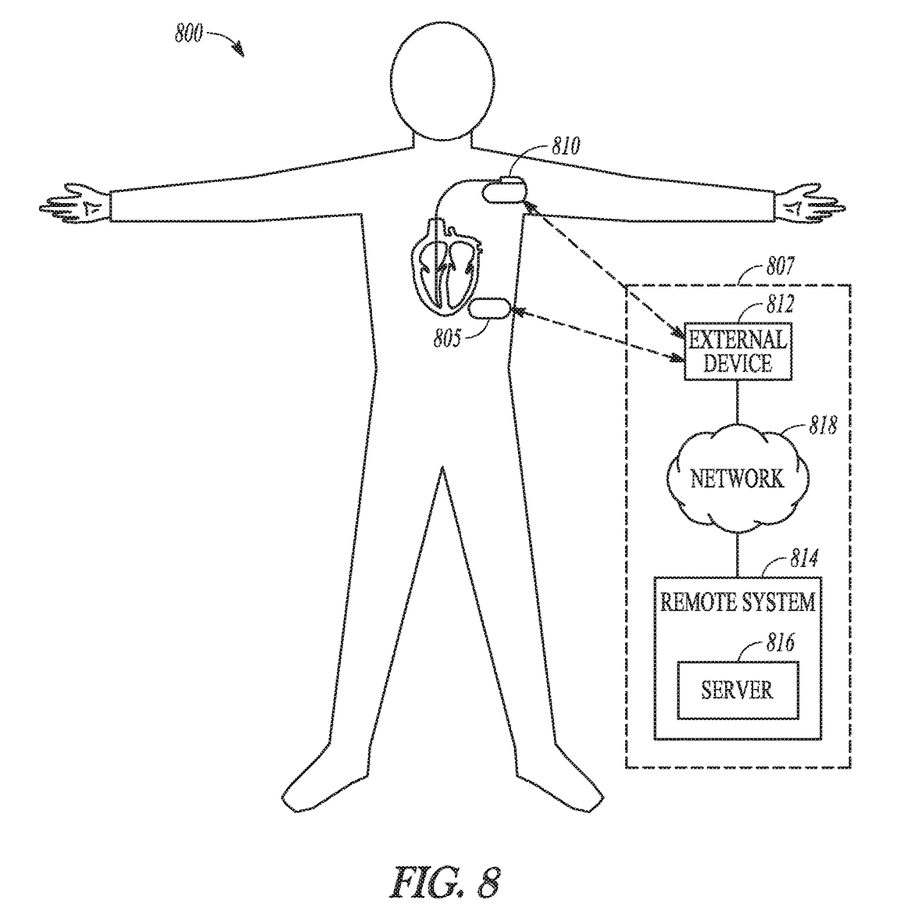
FIG. 8 is an illustration of portions of an example of a medical device system.

FIG. 8 is an illustration of portions of an example of a medical device system 800. The system 800 may include a conventionally implantable medical device 810 or a subcutaneously implantable medical device 805. The implantable medical device can include a communication circuit (e.g., a telemetry circuit) to communicate the indication of AF to a communication system 807. The communication system 807 can include an external communication device 812 and a remote system 814 that communicates with the external communication device 812 via a network 818 (e.g., the internet, a proprietary computer network, or a cellular phone network). The remote system 814 may include a server 816 remotely located from the external communication device 812 and the subject to perform patient management functions. The external communication device 812 may include a programmer to program therapy parameters of a device-based therapy provided by the implantable medical device. One or both of the external communication device 812 and the remote system 814 may include a display to present the indication of AF to a user, such as a clinician.

Correct identification of AF can be useful to a physician in treatment of patients with heart failure (HF). Accurate monitoring of the AF burden allows for effective titration of medication to the patient. The devices, systems, and method described herein enable effective device-based monitoring and trending of AF even though dedicated device-based atrial sensing is not provided.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
 a heart sound sensing circuit configured to generate a sensed heart sound signal representative of at least one heart sound of a subject; and
 an arrhythmia detection circuit configured to:
 monitor time intervals that include a fiducial of at least one heart sound of the subject;
 monitor ventricular depolarization (V-V) intervals;
 calculate a value of variability of the V-V intervals and calculate a value of variability of the time intervals: and
 generate an indication of atrial fibrillation (AF) when the calculated values indicate that a change in variability of the V-V intervals is greater than a change in variability of the time intervals.

2. The system of claim 1, wherein the arrhythmia detection circuit is configured to:
 monitor time intervals between S1 heart sounds and S2 heart sounds (S1-S2 intervals); calculate a value of variability of the S1-S2 intervals; and generate the indication of AF when the calculated values indicate that the change in variability of the V-V intervals is greater than a change in variability of the S1-S2 intervals.

3. The system of claim 1, including a cardiac signal sensing circuit configured to generate a sensed cardiac signal representative of electrical cardiac activity of the subject, wherein the arrhythmia detection circuit is configured to: detect an R-wave in the cardiac signal; monitor intervals between R-waves and S2 heart sounds (R-S2 intervals) using the cardiac signal and the heart sound signal; calculate a value of variability of the R-S2 intervals; and generate the indication of AF when the calculated values indicate that a change in variability of the V-V intervals is greater than a change in variability of the R-S2 intervals.

4. The system of claim 3, wherein the cardiac signal sensing circuit and arrhythmia detection circuit are implantable subcutaneously and includes electrodes configured to sense cardiac signals absent direct cardiac contact with the subject.

5. The system of claim 1, including a cardiac signal sensing circuit configured to generate a sensed cardiac signal representative of electrical cardiac activity of the subject, wherein the arrhythmia detection circuit is configured to: detect a Q-wave in the cardiac signal; monitor intervals between Q-waves and S1 heart sounds (Q-S1 intervals) using the cardiac signal and the heart sound signal; calculate a value of variability of the Q-S1 intervals; and generate the indication of AF when the calculated values indicate that a change in variability of the V-V intervals is greater than a change in variability of the Q-S1 intervals.

6. The system of claim 1, wherein the time intervals that include the fiducial of at the least one heart sound represent systolic portions of the V-V intervals, wherein a systolic portion of a V-V interval is a sub-interval of the V-V interval associated with cardiac systole; and wherein the arrhythmia detection circuit is configured to calculate a value of variability of the systolic portion of the V-V intervals; and generate the indication of AF when the calculated values indicate that a change in variability of the V-V intervals is greater than a change in variability of the systolic portion of the V-V intervals.

7. The system of claim 1, wherein the arrhythmia detection circuit is configured to change a device-based electrical therapy or device-based drug therapy in response to the generated indication of AF.

8. The system of claim 1, wherein the arrhythmia detection circuit is configured to generate the indication of AF when the calculated values indicate that the change in variability of the V-V intervals is greater than the change in variability of the time intervals and the change in variability of the V-V intervals exceeds a first specified arrhythmia detection variability change value threshold.

9. The system of claim 1 wherein the arrhythmia detection circuit is configured to calculate a ratio of the value of variability of the V-V intervals to the value of variability of the time intervals that include the fiducial of the at least one heart sound, and generate the indication of AF when the calculated ratio indicates that the change in variability of the V-V intervals is greater than the change in variability of the time intervals.

10. The system of claim 1, wherein the arrhythmia detection circuit is configured to detect when the change in the variability of the V-V intervals satisfies a specified arrhythmia detection variability change value within a specified time duration, and compare the value of variability of the V-V intervals to the value of variability of the time intervals that include the fiducial of the at least one heart sound when the change in the variability of the V-V intervals satisfies the specified arrhythmia detection variability change value.

11. The system of claim 1, wherein the arrhythmia detection circuit is configured to detect when at least a portion of the V-V intervals satisfies an arrhythmia detection threshold interval, and generate the indication of AF when the V-V intervals satisfies an arrhythmia detection threshold interval and when the calculated values indicate that the change in variability of the V-V intervals is greater than the change in variability of the time intervals that include the fiducial of the at least one heart sound.

12. The system of claim 1, wherein the arrhythmia detection circuit is configured to calculate a value of AF burden for the subject according to the indication of AF.

13. The system of claim 1, including a therapy circuit configured to provide electrical cardioverter/defibrillation therapy to a single ventricle of the subject according to monitored V-V intervals.

14. A method of operating a medical device, the method comprising:
monitoring ventricular depolarization (V-V) intervals of a subject;
monitoring time intervals that include a fiducial of at least one heart sound of the subject;
calculating a value of variability of the V-V intervals;
calculating a value of variability of the time intervals that include the fiducial of the least one heart sound; and
generating, with the medical device, an indication of atrial fibrillation (AF) when the calculated values indicate that a change in variability of the V-V intervals is greater than a change in variability of the time intervals.

15. The method of claim 14, wherein monitoring time intervals that include a fiducial of at least one heart sound includes monitoring time intervals between S1 heart sounds and S2 heart sounds (S1-S2 intervals); wherein calculating a value of variability of the time intervals includes calculating a value of variability of the S1-S2 intervals; and wherein generating the indication of AF includes generating the indication when the calculated values indicate that the change in variability of the V-V intervals is greater than a change in variability of the S1-S2 intervals.

16. The method of claim 14, wherein monitoring time intervals that include a fiducial of at least one heart sound includes monitoring time intervals between R-waves and S2 heart sounds (R-S2 intervals) using a sensed cardiac signal and a heart sound signal; wherein calculating a value of variability of the time intervals includes calculating a value of variability of the R-S2 intervals; and wherein generating the indication of AF includes generating the indication of AF when the calculated values indicate that a change in variability of the V-V intervals is greater than a change in variability of the R-S2 intervals.

17. The method of claim 14, wherein monitoring time intervals that include a fiducial of at least one heart sound includes monitoring time intervals between Q-waves and S1 heart sounds (Q-S1 intervals) using the cardiac signal and the heart sound signal; wherein calculating a value of variability of the time intervals includes calculating a value of variability of the Q-S1 intervals; and wherein generating the indication of AF includes generating the indication of AF when the calculated values indicate that a change in variability of the V-V intervals is greater than a change in variability of the Q-S1 intervals.

18. The method of claim 14, wherein monitoring time intervals that include a fiducial of at least one heart sound includes monitoring time intervals that represent the systolic portions of the V-V intervals, wherein a systolic portion of a V-V interval is a sub-interval of the V-V interval associated with cardiac systole; wherein calculating a value of variability of the time intervals includes calculating a value of variability of the systolic portion of the V-V intervals; and wherein generating the indication of AF includes generating the indication of AF when the calculated values indicate that a change in variability of the V-V intervals is greater than a change in variability of the systolic portion of the V-V intervals.

19. The method of claim 14, including generating the indication of AF when the calculated values indicate that the change in variability of the V-V intervals is greater than the change in variability of the time intervals and the change in variability of the V-V intervals exceeds a first specified arrhythmia detection variability change value threshold.

20. The method of claim 14, including changing a device-based electrical therapy or device-based drug therapy in response to the generated indication of AF.

* * * * *